United States Patent
Mäntyjärvi et al.

(10) Patent No.: US 7,685,433 B2
(45) Date of Patent: *Mar. 23, 2010

(54) RECOGNITION OF LIVE OBJECT IN MOTION

(75) Inventors: Jani Mäntyjärvi, Oulunsalo (FI); Mikko Lindholm, Oulu (FI); Heikki Ailisto, Oulu (FI)

(73) Assignee: Valtion teknillinen tutkimuskeskus, Espoo (FI)

( * ) Notice: Subject to any disclaimer, the term of this patent is extended or adjusted under 35 U.S.C. 154(b) by 1230 days.

This patent is subject to a terminal disclaimer.

(21) Appl. No.: 11/222,113

(22) Filed: Sep. 9, 2005

(65) Prior Publication Data

US 2006/0080551 A1  Apr. 13, 2006

(30) Foreign Application Priority Data

Sep. 13, 2004  (FI) ................... 20045336

(51) Int. Cl.
*H04K 1/00* (2006.01)
*G06F 11/00* (2006.01)
*H04L 9/32* (2006.01)

(52) U.S. Cl. .................... 713/186; 726/27; 726/28; 726/29; 726/30; 380/229; 380/230; 380/231; 380/232

(58) Field of Classification Search .................. 713/186
See application file for complete search history.

(56) References Cited

U.S. PATENT DOCUMENTS

2002/0107649 A1 * 8/2002 Takiguchi et al. ............. 702/75

FOREIGN PATENT DOCUMENTS

| JP | 2001-190527 |   | 7/2001 |
|---|---|---|---|
| JP | 2005-78228 |   | 3/2005 |
| WO | WO 2004040501 | * | 5/2004 |

OTHER PUBLICATIONS

Mantyjarvi et al., "Identifying Users of Portable Devices from Gait Pattern with Accelerometers", IEEE International Conference on Acoustics, Speech, and Signal Processing, Mar. 18-23, 2005, vol. 2, pp. 973-976.
Mantyjarvi et al., "Recognizing Human Motion with Multiple Acceleration Sensors", IEEE International Conference on Systems, Man, and Cybernetics, Oct. 7-10, 2001, vol. 2, pp. 747-752.

* cited by examiner

*Primary Examiner*—Longbit Chai
(74) *Attorney, Agent, or Firm*—Young & Thompson

(57) ABSTRACT

Movement of a living object is measured by a movement sensor carried by one living object at a time for forming one measurement signal per one living object. The measurement signal is compared with a predetermined reference signal which may be measured from a known living object in a similar way. A recognition operation is performed based on the comparison between the measurement signal and the predetermined reference signal, the recognition operation resulting in recognition or non-recognition.

51 Claims, 6 Drawing Sheets

RECOGNITION OF LIVE OBJECT IN MOTION

FIELD

The invention relates to methods of identifying a carrier of a portable device, forming signals for recognizing a living object which is moving, performing a recognition operation relating to a living object which is moving, controlling the use of a device relating to a living object which is moving, and to a portable device carried by a carrier, a portable device carried by a moving carrier, to a system including a portable device carried by a moving carrier, and to computer program products relating to the methods.

BACKGROUND

Portable electronic devices, such as smart phones and personal digital assistants (PDAs), wearable computers, intelligent clothing and smart artefacts are becoming a part of our everyday environment. Protecting them is becoming more and more important, not only because of the value of the devices themselves, but also because there are means of storing valuable and discrete data and their capability for communication, remote transactions, including m-commerce (mobile commerce) and m-banking (mobile banking).

The authentication of a user of an electronic device may be carried out by using a password, such as a PIN code (Personal Identification Number) which may be difficult to remember. Alternatively or additionally, some devices contain fingerprint-based user authentication systems.

Yet, the protection of these devices is usually poor, especially in "on" state, when not even the PIN code nor the fingerprint authentication protects the information and the device. Clearly, a need exists for an unobtrusive, implicit security mechanism.

BRIEF DESCRIPTION OF THE INVENTION

An object of the invention is to provide improved methods, portable device, system and computer programs relating to recognition of a living object in motion.

According to an aspect of the invention, there is provided a method of identifying a carrier of a portable device, the method comprising identifying a carrier of a device by a signal provided by an acceleration sensor of the device carried by the carrier, the identification and the signal analysis being based on at least one of the following: cross correlation, amplitude histogram features, Fourier coefficients, structural pattern recognition.

According to another aspect of the invention, there is provided a method of forming signals for recognizing a living object which is moving, the method comprising measuring movement of at least one predetermined living object by at least one movement sensor carried by one living object at a time for forming at least one reference signal per one living object; and measuring movement of at least one living object by the at least one movement sensor carried by one living object at a time for forming at least one measurement signal per one living object.

According to another aspect of the invention, there is provided a method of performing a recognition operation relating to a living object which is moving, the method comprising measuring movement of at least one living object by a movement sensor carried by one living object at a time for forming at least one measurement signal per one living object; comparing the at least one measurement signal with at least one predetermined reference signal; and performing a recognition operation based on the comparison between the at least one measurement signal and the at least one predetermined reference signal, the recognition operation resulting in recognition or non-recognition.

According to another aspect of the invention, there is provided a method of controlling use of a device relating to a living object which is moving, the method comprising measuring movement of at least one user by a movement sensor carried by one user at a time for forming at least one movement signal per living object; comparing the at least one movement signal with at least one predetermined reference signal; performing a recognition operation based on the comparison between the at least one movement signal and the at least one predetermined reference signal, the recognition operation resulting in recognition or non-recognition of the living object; and controlling the use of the device by the living object based on the result of the recognition operation.

According to another aspect of the invention, there is provided a portable device carried by a carrier, the device comprising an acceleration sensor providing an acceleration signal of the carrier; a recognizer configured to identify the carrier of the device by a signal provided by the acceleration sensor, the identification and the analysis of which the signal being based on at least one of the following: cross correlation, amplitude histogram features, Fourier coefficients, structural pattern recognition.

According to another aspect of the invention, there is provided a portable device carried by a moving carrier, the device comprising a movement sensor configured to measure movement of each predetermined living object of at least one living object by a movement sensor carried by one living object at a time for forming at least one reference signal per one living object; measure movement of each living object of at least one living object by a movement sensor carried by one living object at a time for forming at least one measurement signal per one living object; and a memory for storing the at least one reference signal.

According to another aspect of the invention, there is provided a system including a portable device carried by a moving carrier, the device comprising at least one movement sensor configured to measure movement of each predetermined living object of at least one living object by a movement sensor carried by one living object at a time for forming at least one reference signal per one living object; and measure movement of each living object of at least one living object by a movement sensor carried by one living object at a time for forming at least one measurement signal per one living object.

According to another aspect of the invention, there is provided a computer program product encoding a computer program of instructions for executing a computer process for forming signals for recognizing a living object which is moving, the process comprising: measuring movement of at least one predetermined living object by at least one movement sensor carried by one living object at a time for forming at least one reference signal per one living object; and measuring movement of at least one living object by the at least one movement sensor carried by one living object at a time for forming at least one measurement signal per one living object.

According to another aspect of the invention, there is provided a computer program product encoding a computer program of instructions for executing a computer process for performing a recognition operation relating to a living object which is moving, the process comprising: measuring movement of at least one living object by a movement sensor carried by one living object at a time for forming at least one movement signal per one living object; comparing the at least one movement signal with at least one predetermined reference signal; and performing a recognition operation based on the comparison between the at least one movement signal and the at least one predetermined reference signal, the recognition operation resulting in recognition or non-recognition.

According to another aspect of the invention, there is provided a computer program product encoding a computer program of instructions for executing a computer process for controlling the use of a device relating a living object which is moving, the process comprising: measuring movement of at least one user by a movement sensor carried by one user at a time for forming at least one movement signal per one user; comparing the at least one movement signal with at least one predetermined reference signal; performing a recognition operation based on the comparison between the at least one movement signal and the at least one predetermined reference signal, the recognition operation resulting in recognition or non-recognition of the user; and controlling the use of the device based on the result of the recognition operation.

According to another aspect of the invention, there is provided a computer program distribution medium readable by a computer and encoding a computer program of instructions for executing a computer process for forming signals for recognizing a living object which is moving, the process comprising: measuring movement of at least one predetermined living object by at least one movement sensor carried by one living object at a time for forming at least one reference signal per one living object; and measuring movement of at least one living object by the at least one movement sensor carried by one living object at a time for forming at least one measurement signal per one living object.

According to another aspect of the invention, there is provided a computer program distribution medium readable by a computer and encoding a computer program of instructions for executing a computer process for performing a recognition operation relating to a living object which is moving, the process comprising: measuring movement of at least one living object by a movement sensor carried by one living object at a time for forming at least one movement signal per one living object; comparing the at least one movement signal with at least one predetermined reference signal; and performing a recognition operation based on the comparison between the at least one movement signal and the at least one predetermined reference signal, the recognition operation resulting in recognition or non-recognition.

According to another aspect of the invention, there is provided a computer program distribution medium readable by a computer and encoding a computer program of instructions for executing a computer process for controlling the use of a device carried by a moving user, the process comprising: measuring movement of at least one user by a movement sensor carried by one user at a time for forming at least one movement signal per one user; comparing the at least one movement signal with at least one predetermined reference signal; performing a recognition operation based on the comparison between the at least one movement signal and the at least one predetermined reference signal, the recognition operation resulting in recognition or non-recognition of the user; and controlling the use of the device based on the result of the recognition operation.

The invention provides several advantages. The solution is unobtrusive, not requiring an explicit data input, e.g. PIN or finger print. The user of the system cannot forget the password. A carrier's behaviour is difficult to imitate by a possible unauthorized user. Expenses of implementation (device, software, assembly, etc.) and the possibility of misidentification are small.

LIST OF DRAWINGS

In the following, the invention will be described in greater detail with reference to embodiments and the accompanying drawings, in which FIG. 1 shows a living object with portable devices including movement sensors;

DESCRIPTION OF EMBODIMENTS

While video-based gait biometrics is targeted for surveillance, security and forensic applications, the present solution may be aimed at protecting personal devices against illicit use. The present solution is well-suited for use in electronic devices such as, for example, mobile phones, personal digital assistants (PDAs), wearable computers, intelligent clothing or smart artefacts. The present solution can be applied even to portable weapons such as hand guns, the solution not, however, being restricted to these examples.

Figure 1:
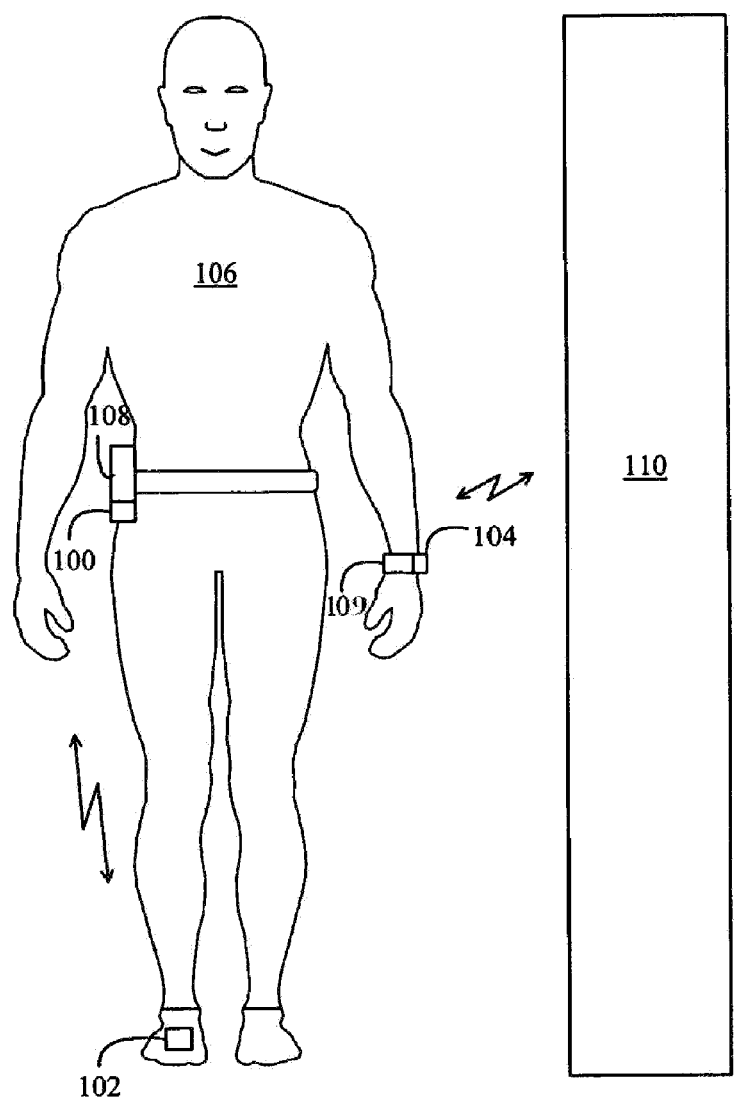

FIG. 1 shows a living object which is a carrier 106 of movement sensors 100, 102, 104. In the present solution, the carrier 106 may carry only one movement sensor, but it is also possible that the carrier 106 carries a plurality of movement sensors. The carrier 106 is a living organism, such as a human being or an animal, for example, a cat, a dog, a horse, etc. A movement sensor 100 may be a part of a portable electrical device 108, such as a mobile phone, which may be fixed to a belt around the waist. A movement sensor 102 may also be fixed, for example, to a shoe. A movement sensor 104 may also be in conjunction with a wrist watch 109. A movement sensor may also communicate with a separate device 110 which may also be considered as a remote device being placed at a variable distance away from the movement sensor(s). The operation of the separate device 110 may be controlled by a signal(s) received by the separate device 110. The separate device 110 may be, for example, a door which is opened if the carrier of the movement sensors is an acceptable carrier and which remains closed if the carrier is an unacceptable carrier.

Each of the movement sensors 100, 102, 104 may be an acceleration sensor which may perform inertial sensing, for example, of gait characteristics. The acceleration sensors may measure acceleration of the trunk as a function of time during gait. Additionally or alternatively, the acceleration sensors may measure acceleration of a limb or limbs, for instance, during walking, running, dancing, or any other movement. Each of the movement sensors 100, 102, 104 may be a triaxial accelometer which may provide an acceleration signal in three dimensions. However, the movement sensors may also measure acceleration only in one dimension or in two dimensions.

The movement sensors may output velocity or speed of the carrier. The velocity can be obtained by integrating the acceleration over time, or the velocity may be obtained by analysing step signals.

The sensor 100 to 104 with a battery and a transmitter may be placed separately from the electrical device 108, 110. The sensor 100 to 104 may communicate wirelessly with the electrical device 108, 110 and the electrical device 108, 110 may be configured such that when the electrical device 108, 110 does not receive a signal from the sensor 100 to 104 the electrical device 108, 110 stops functioning. The reason for receiving no signal may be too long a distance. For example, if a proper user of a computer wears this kind of sensor and an improper user takes (steals) the computer away, the improper user cannot use the computer. Also, if an improper user takes both the computer and the sensor, the improper user cannot use the computer because the signals transmitted from the sensor imply an attempt at unauthorized use.

Figure 2:
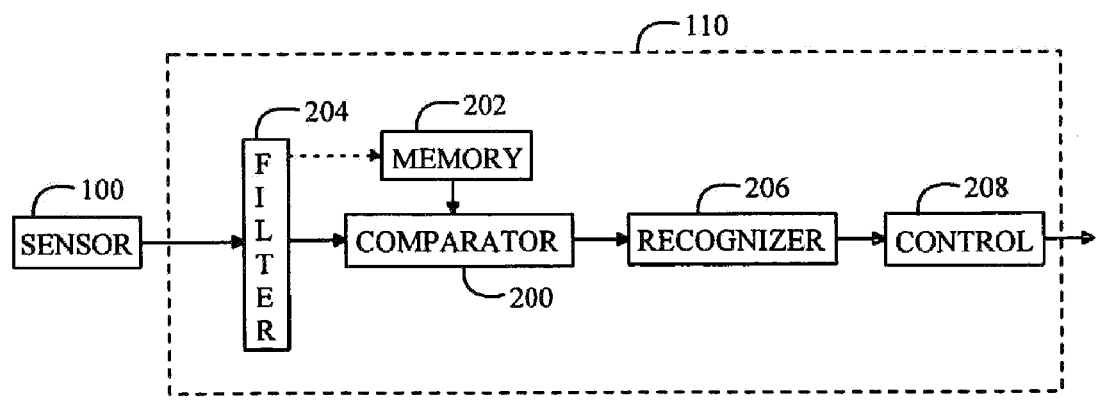
FIG. 2 illustrates a system recognizing the living object.

With reference to FIG. 2, examine a block diagram of the present system. The system may include at least one movement sensor 100, a comparator 200, memory 202, a filter 204, a recognizer 206 and a control 208. Each of the parts 200 to 208 may be situated in a portable device or at least one of the parts 200 to 208 may be situated in a separate device 110, outside the portable device. The parts may communicate through a wire or wirelessly. At first, a group of carriers of the sensor 100 can be determined or the group can be otherwise known. The group may include only one predetermined carrier or the group may include more than one carrier. During enrolment, the movement sensor 100 can be used to measure the movement of each carrier of the predetermined group one by one for forming at least one reference signal per one carrier. The measured signal may be filtered in the filter 204. The at least one reference signal may be stored in a memory 202. The memory 202 for storing at least one reference signal may be in a portable device (such as mobile phone) carried by the carrier. The device may also include at least one movement sensor. Alternatively, the memory 202 for storing at least one reference signal may be in a remote device not carried by the carrier.

After the at least one reference signal has been stored in the memory 202, any carrier carrying the movement sensors can be recognised and categorized. The recognition may mean identification or verification. In a similar manner to that of forming a reference signal, movement of at least one carrier is measured by a movement sensor 100 carried by one carrier at a time. At least one movement signal per one carrier is formed. The comparator 200 may compare the at least one movement signal with at least one predetermined reference signal. A recognition operation may be performed in the recogniser 206 based on the comparison. The recognition operation may result in recognition or non-recognition. The recognition means that the measurement signal and the reference signal were found to be similar enough and the source of the measurement signal can be considered the same as the source of the reference signal. That is, at least one of the measurement signals came from the same carrier as the reference signal. Control of the portable device or a remote device may be performed by the controller 208.

Figure 3:
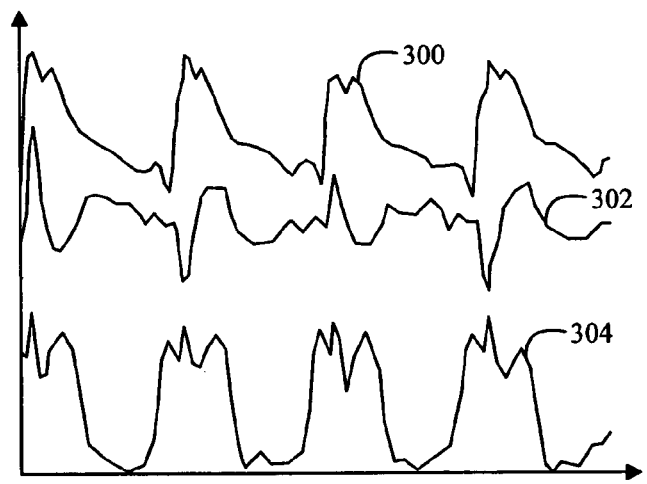
FIG. 3 illustrates signals in acceleration measurement.

Before going further into details let us take a look at the movement signals. FIG. 3 shows signals in acceleration measurements. The vertical axis represents strength of acceleration in an arbitrary scale, and the horizontal axis represents time. In this example, a human carrier has walked with a portable device including a triaxial acceleration sensor. The portable device can be worn on a belt, in a way similar to carrying a mobile phone or a PDA in a holster. An output signal of an accelerometer may be recorded at a frequency of 256 Hz using a computer having computer programs for signal processing.

Each movement signal 300 to 304 can be measured in an independent dimension with respect to others and the movement signals have been shifted with respect to each other so that they can be plotted separately in a chart. However, amplitude variation in the signals is in a direct relation to variation in the acceleration. The movement signal 300 represents acceleration in the horizontal direction along the direction of walking, i.e. forward direction, and the movement signal 304 represents acceleration in the vertical direction. The movement signal 302 represents acceleration in the horizontal direction perpendicular to the walking direction. A walking direction is the direction at which the velocity vector of the carrier points at. It can be seen in FIG. 3 that steps cause a rather regular variation in the acceleration in each dimension.

Figure 4:
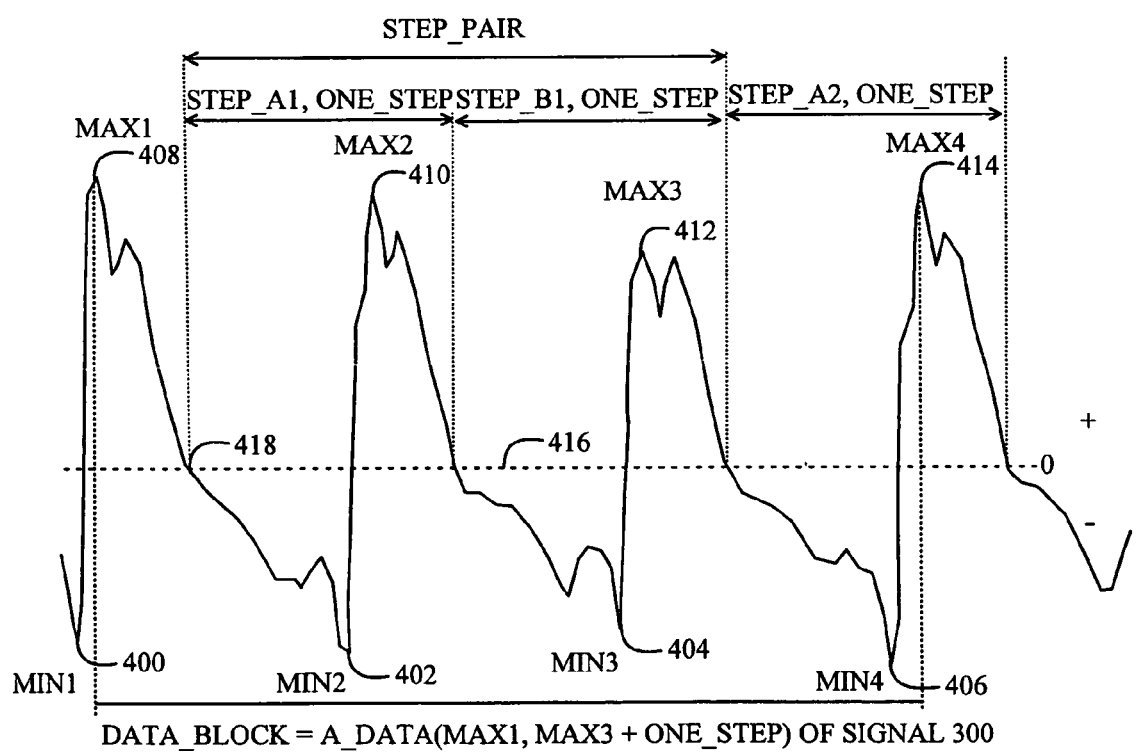
FIG. 4 illustrates a measured signal.
Figures 5A, 5B, 5C, 5D:
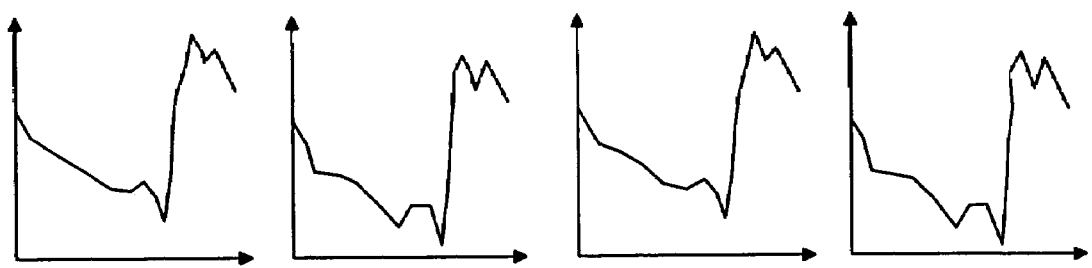
FIG. 5A illustrates a step in one dimension.
FIG. 5B illustrates a step in one dimension.
FIG. 5C illustrates a step in one dimension.
FIG. 5D illustrates a step in one dimension.
Figures 6A, 6B, 6C, 6D:
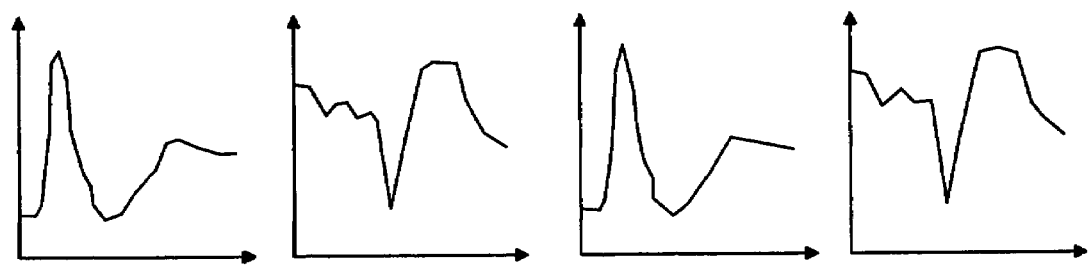
FIG. 6A illustrates a step in one dimension.
FIG. 6B illustrates a step in one dimension.
FIG. 6C illustrates a step in one dimension.
FIG. 6D illustrates a step in one dimension.
Figures 7A, 7B, 7C, 7D:
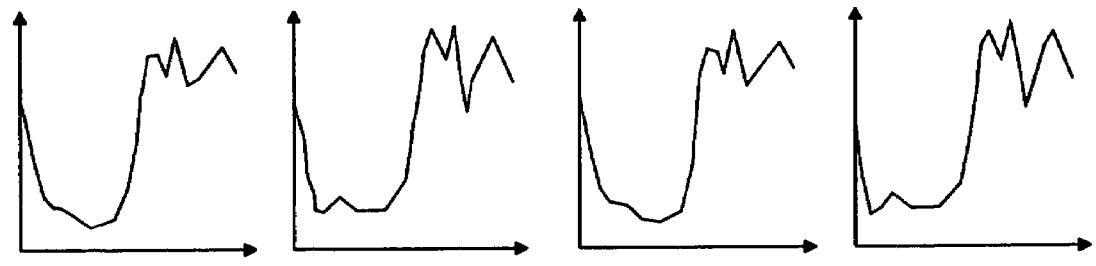
FIG. 7A illustrates a step in one dimension.
FIG. 7B illustrates a step in one dimension.
FIG. 7C illustrates a step in one dimension.
FIG. 7D illustrates a step in one dimension.

Referring to FIG. 4, examine the movement signal 300 relating to gait and enrolment a little bit closer. Each movement signal 300 to 304 may be filtered in the filter 204 by dividing each movement signal 300 to 304 into partial signals which represent separate steps. In general, the measured signal (for forming a reference signal or a measurement signal) received from the movement sensor can be divided into partial signals, each relating to different movements. Since the right and left steps are usually not identical, it is useful to process them separately, as "a" and "b" step signals. However, the step signals do not need to be identified as "right" and "left". Separate step signals can be found in all measurement signals, for example, by searching for local minima 400 to 406 and maxima 408 to 414. Signals of both kinds of steps may be normalized in length and amplitude. An average level 416 where no forces act on the carrier may also be determined in the filter 204. When a plurality of step signals (of one leg) is available, an averaged step signal may be formed in the filter 204. A movement signal made of the averaged step signal(s) may form a basis of a biometric template, i.e. a reference signal, which can also be called a gait code. The horizontal signal 302 is not necessarily used, since it has proved to be less permanent than the two other movement signals, and it may be filtered out in the filter 204. However, it may be taken into account and processed similarly.

Each Figure from 5A to 5D shows a separate step extracted from the movement signal 300 in FIGS. 3 and 4. Each Figure from 6A to 6D shows a separate step extracted from the movement signal 302 in FIG. 3. Similarly, each Figure from 7A to 7D shows a separate step signal extracted from the movement signal 304 in FIG. 3.

The separation of the step signals may be performed as follows. The separation takes place in the filter 204. An initial average length of one step, One_Step, should first be determined from acceleration data, A_Data. This may be decided by a frequency analysis based on fast fourier transform or by experience. Then, a first minimum point 400, Min1, within first One_Step in the movement signal 300 can be searched for. The measurement signal 300 is easy to use, since it has a relatively unambiguous wave form. Then, a first local maximum point 408, Max1, can be searched for. Max1 may be used as the starting point of the search for Step_Pair (and also for step a). Max1 should occur somewhere between Min1 and (Min1+One_Step), since the maximum part of either step a or b resides between two consecutive minima. A second maximum point 410, Max2, marks the location at which the search for the starting point of step b (end point of step a) begins and a third maximum point 412, Max3, is, in a similar manner, the preliminary end point of Step_Pair (and the end point of step b). The maximum point 410, Max2, can be found by finding the maximum value from Max1+(1−α)*One_Step to (1+α)*One_Step, where the weight α can be a small number less than 1, for example 0.00001 to 0.5. The weight α can be about 0.1 when gait is analysed. The other maximum points 412, Max3, can be found in a corresponding way.

If the local maxima, Max1, Max2, Max3 are unambiguous, we can separate all the following Step_Pairs in all signals 300 to 304 as explained above. Unfortunately, there may be one or more side peaks nearby the local maxima, which sometimes may turn out to be the local maxima looked for. The same is true for local minima, as well. This makes it difficult to find the equivalent relative Max1, Max2, Max3, Max4 locations and, consequently, the same starting and end points for Step_Pairs. If starting and end points differ, meaningful data averaging for gait code may in practice become impossible.

To overcome this difficulty, descending slopes of the signal following the points Max1, Max2 and Max3 can be used. Points Mean_Point1, Mean_Point2 and Mean_Point3 have the average value of Data_Block and they may be searched for. The length of Data_Block is a three times One_Step long part of the measurement signal 300 inside which one Step_Pair must reside. For one Step_Pair the three consecutive Mean_Points are: the beginning of step a (Mean_Point1), the end of step a or beginning of step b (Mean_Point2), and the end of step b (Mean_Point3). To find Mean_Points the averaged Mean_Data of the Data_Block is needed. Mean_Data can be formed by subtracting the average of Data_Block from Data_Block. The idea is to look for points of transition from a positive to a negative value after Max1, Max2 and Max3.

The descending slope is not the only location where values similar to Mean_Points may exist. Therefore, the search area inside the Mean_Data must be limited. A first mean point 418, Mean_Point1, can be found by determining a shift from a positive value to a negative value within Mean_Data from (Max1+α*One_Step) to (Max1+β*One_Step) where β may be about 0.5. Mean_Point2 and Mean_Point3 are searched for in a similar manner. Now the first Step_Pair, with the limits of steps a and b known, can be confined and the corresponding Step_Pairs of A_Data in the other measurement signals 302 and/or 304 can be separated with the indices of the measurement signal 300 Mean_Points. The process for all the next Step_Pairs is the same except that the length of One_Step is continuously updated and Min1 is no longer needed.

After separation, the step signals may be categorized into Step_a and Step_b signals where Step_a signal represents steps of one leg and a Step_b signal represent steps of another leg. This may take place in the filter 204.

The length of each individual step signal may also be normalized to a desired number of points in the filter 204. The normalization may be such that a step signal includes 256 points which may be achieved by normalizing Step_a and Step_b of each Step_Pair to 128 points. To find a more representative gait code, all the Step_a steps can be correlated against each other and correlation coefficients can be added to form a similarity value, Similarity_aN. Similarity_aN can be formed in the following manner:

$$\text{Similarity\_aN} = \sum_{i=1}^{N} corr(\text{Step\_ai}, \text{Step\_ai}), \quad (1)$$

where corr means cross correlation between step signals Step_ai and Step_ai and where i is an index. The same is carried out for all Step_b steps:

$$\text{Similarity\_bN} = \sum_{i=1}^{N} corr(\text{Step\_bi}, \text{Step\_bi}), \quad (2)$$

i.e. steps relating to another leg and for all signals 300 to 304.

The step signals may be averaged using the best step signals (when step signals are available), or the most representative step signals may be used in the filter 204. The best signal may include a certain percentage of all signals. The step signals may be averaged using, for instance, 60% of the step signals better than others. That is, 60% of the step signals (relating to the same leg) with the highest similarity values are chosen. They may be averaged and the amplitude of the averaged result may be normalized between desired limits, such as [−0.5, +0.5] to form a mean step signal.

Figure 8:
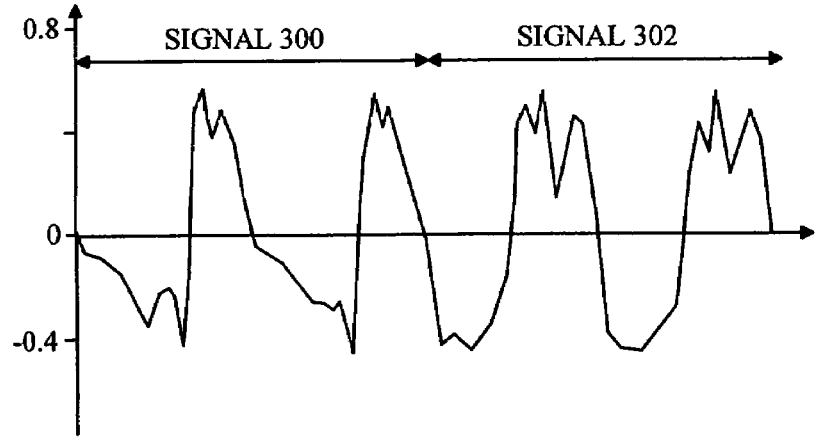
FIG. 8 illustrates concatenation of step signals.
Figures 9A, 9B, 9C, 9D:
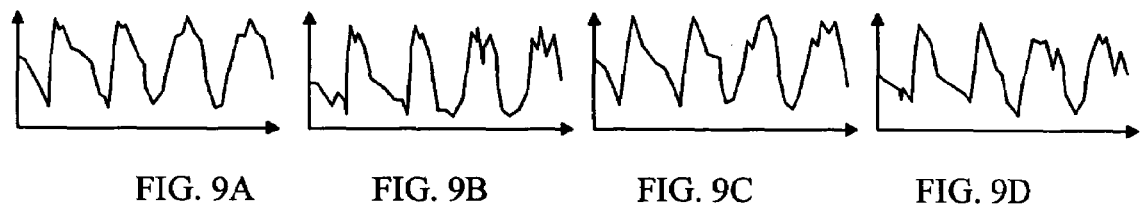
FIG. 9A illustrates a reference signal.
FIG. 9B illustrates a reference signal.
FIG. 9C illustrates a reference signal.
FIG. 9D illustrates a reference signal.

Finally, a biometric template, i.e. a reference signal, or a gait code may be created by concatenating the averaged and normalized step signals a and b of signals 300 to 304 to a gait code vector in the filter 204. The reference signal is shown in FIG. 8.

After forming a reference, a measurement signal can be measured. The measurement signal and the reference signal can be formed similarly. To determinate a carrier, the movement sensor 100 can be used for measuring the movement of each carrier of a group one by one for forming at least one measurement signal per one carrier to be recognized. The measurement signal is formed into the same structure as the reference signal but naturally its shape, amplitude, frequency, etc. may differ from or may be similar to those of the reference signal, depending on the carrier. At least the movement sensor is carried by a carrier who should be recognized. When at least one measurement signal has been measured, a comparison between the measurement signal and the reference signal can be performed.

Since the order of the steps (left-right or vice versa) in the reference signal and in the measurement signal is not known, the reference signal can be formed twice, or the reference signal can be shifted by a period of one step. In general, a plurality of reference signals may be formed such that consecutive reference signals may be shifted with respect to each other by a predetermined offset. In this kind of case, the predetermined offset is the length of one step. If two reference signals are used, a first reference signal can start from Step a1 and a second reference signal can start from Step b1, i.e. one step (One_Step) further. Now the first reference signal is of the form a-b-a-b and the second of the form b-a-b-a, corresponding to a shift of one step. After this "step interchange", the measured movement signal can be reliably compared to both forms of reference signals of all the enrolled persons.

Figure 10:
FIG. 10 illustrates a measured signal.

As FIGS. 9A to 9D and FIG. 10 show, the comparison can be carried out by correlating all the four individual reference signals in FIGS. 9A to 9D separately against the measurement signal in FIG. 10. The four reference signals in FIGS. 9A to 9D have been obtained from four unique carriers. The measurement signal in FIG. 10 may be obtained from a carrier which is one of the carriers providing the measurement signals in FIGS. 9A to 9D, or the carrier may be an outsider. In general, more than one measurement signal may be provided. The comparison can be carried out by cross correlation $$\text{comp} = \text{corr}(\text{Meas}(i), \text{Ref}(i)), \quad (3)$$

where corr means cross correlation between a measurement signal Meas(i) and a reference signal Ref(i) and where i is an index of a signal. Instead of correlation, statistical methods, such as amplitude histogram features, can be used in time domain.

Alternatively or additionally, the process of signals can also be carried out in a domain obtained by convolution integral transforms, such as Fourier transform, Laplace transform, etc. The Fourier transform can be performed by FFT (Fast Fourier Transform). The comparison can be performed using Fourier (or other convolution transform) coefficients.

Moreover, the comparison can also be based on shapes of the measurement signal and the reference signal, and hence, for instance, structural pattern recognition may be used.

Because steps or other regular movements have variation, they do not in reality start and end exactly at estimated moments. Hence, cross correlation may be performed a plurality of times such that a measurement signal and a reference signal are each time shifted with respect to each other by a different offset. The phase shifts can be predetermined. Usually the phase shifts are small compared to the signal length or to a cycle length i.e. length of one step. The largest value of the correlation can be considered to represent the similarity between the signals.

When the similarity, i.e. correlation is high enough the measurement signal and the reference signal can be considered to originate from the same carrier. The measurement signal in FIG. 10 can be found to be similar enough to the reference signal in FIG. 9D. The correlation coefficients of signals measured in different dimensions can be averaged by giving a figure of similarity C. The carrier of the measurement signal providing the largest similarity can always be recognized as a source of the measurement signal.

Hence, the living object whose the at least one measurement signal provides the largest similarity to the at least one reference signal of a desired living object can be determined as a desired living object. Similarly, a living object whose the at least one measurement signal provides the largest similarity to the at least one reference signal of an undesired living object can be determined as an undesired living object.

If a threshold is used, a living object whose the at least one measurement signal provides the largest similarity to the at least one reference signal of a desired living object, the similarity being greater than a predetermined threshold, can be determined as a desired living object. Correspondingly, a living object whose the at least one measurement signal provides the largest similarity to the at least one reference signal of an undesired living object, the similarity being greater than a predetermined threshold, can be determined as an undesired living object.

If the carrier does not belong to a group of those whose reference signal is known, the recognition based on the largest similarity leads to a wrong recognition. Thus, to improve the recognition, a threshold may be introduced. If the similarity C is larger than a pre-set threshold T, recognition can be considered correct, otherwise the recognition operation may result in non-recognition. Accordingly, the carrier may be recognized, for example, as an acceptable carrier or a non-acceptable carrier of the portable device.

As shown in FIG. 1, the carrier may carry many movement sensors on different parts of the body. Each part of the body moves uniquely with respect to other parts of the same carrier and also with respect to same parts of other carriers. Hence, the recognition of the carrier can be improved by combining the results of several comparisons or recognition operations. For example, for recognizing a carrier as acceptable, all measurement signals should match the reference signals of the same reference carrier. Otherwise the carrier can be determined not recognized (non-acceptable). Additionally, a threshold can be used. Then, all measurement signals should match the reference signals of the same reference carrier better than the threshold.

The present solution can be used for continuous authentication, verification or identification of a carrier of a portable device. It can be used for tracing back the carriers of a portable device. For example, if a portable computer is given to a certain person for a predetermined period of time, it can later be traced whether the person to whom the computer was given was the only user or whether he/she passed on the computer to another user.

Figure 11:
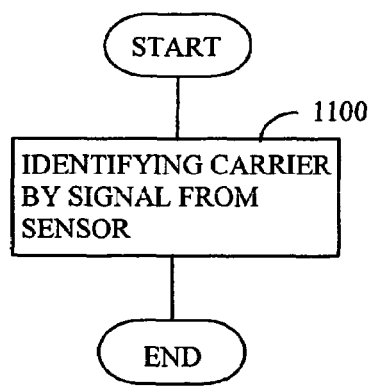
FIG. 11 illustrates a flow chart of a method of identifying a carrier of a portable device.

FIG. 11 shows a flow chart of a method of identifying a carrier of a portable device. In step 1100, a carrier of a device is identified by a signal provided by an acceleration sensor of the device carried by the carrier, the identification and the signal analysis being based on at least one of the following: cross correlation, amplitude histogram features, Fourier coefficients, structural pattern recognition.

Figure 12:
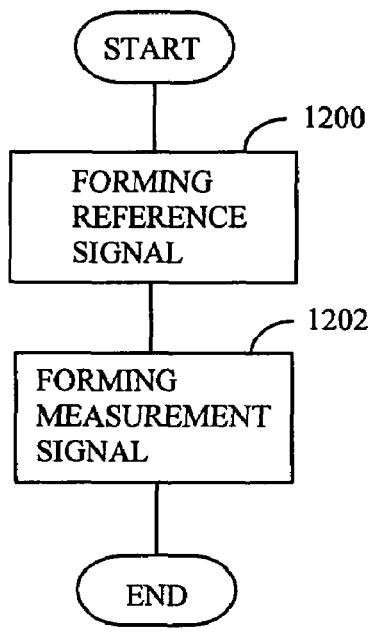
FIG. 12 illustrates a flow chart of a method of forming signals for recognizing a living object which is moving.

FIG. 12 shows a flow chart of a method of forming signals for recognizing a living object which is moving. In step 1200, movement of at least one predetermined living object is measured by at least one movement sensor carried by one living object at a time for forming at least one reference signal per one living object. In step 1202, movement of at least one living object is measured by the at least one movement sensor carried by one living object at a time for forming at least one measurement signal per one living object.

Figure 13:
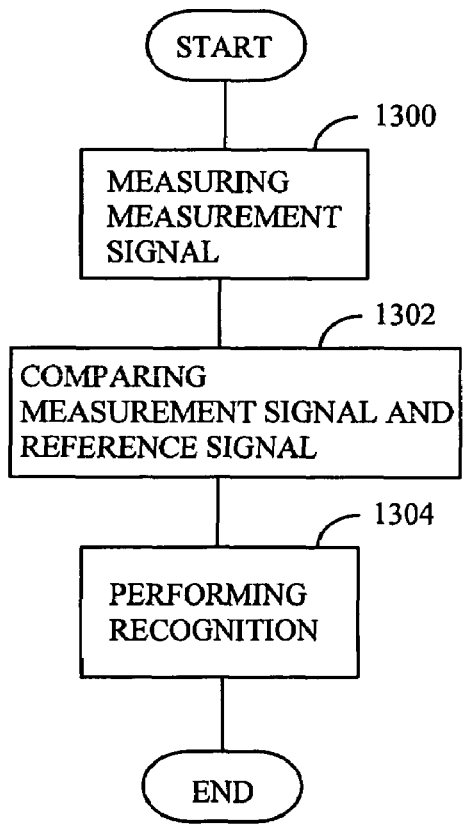
FIG. 13 illustrates a flow chart of a method of performing a recognition operation relating to a living object which is moving.

FIG. 13 shows a flow chart of a method of performing a recognition operation relating to a living object which is moving. In step 1300, movement of at least one living object is measured by a movement sensor carried by one living object at a time for forming at least one measurement signal per one living object. In step 1302, the at least one measurement signal is compared with at least one predetermined reference signal. The comparison is based on similarity of signals. Their shape, distribution of frequencies, distribution of amplitudes, phases and so on may be compared. In step 1304, a recognition operation based on the comparison between the at least one measurement signal and the at least one predetermined reference signal is performed, the recognition operation resulting in recognition or non-recognition.

Figure 14:
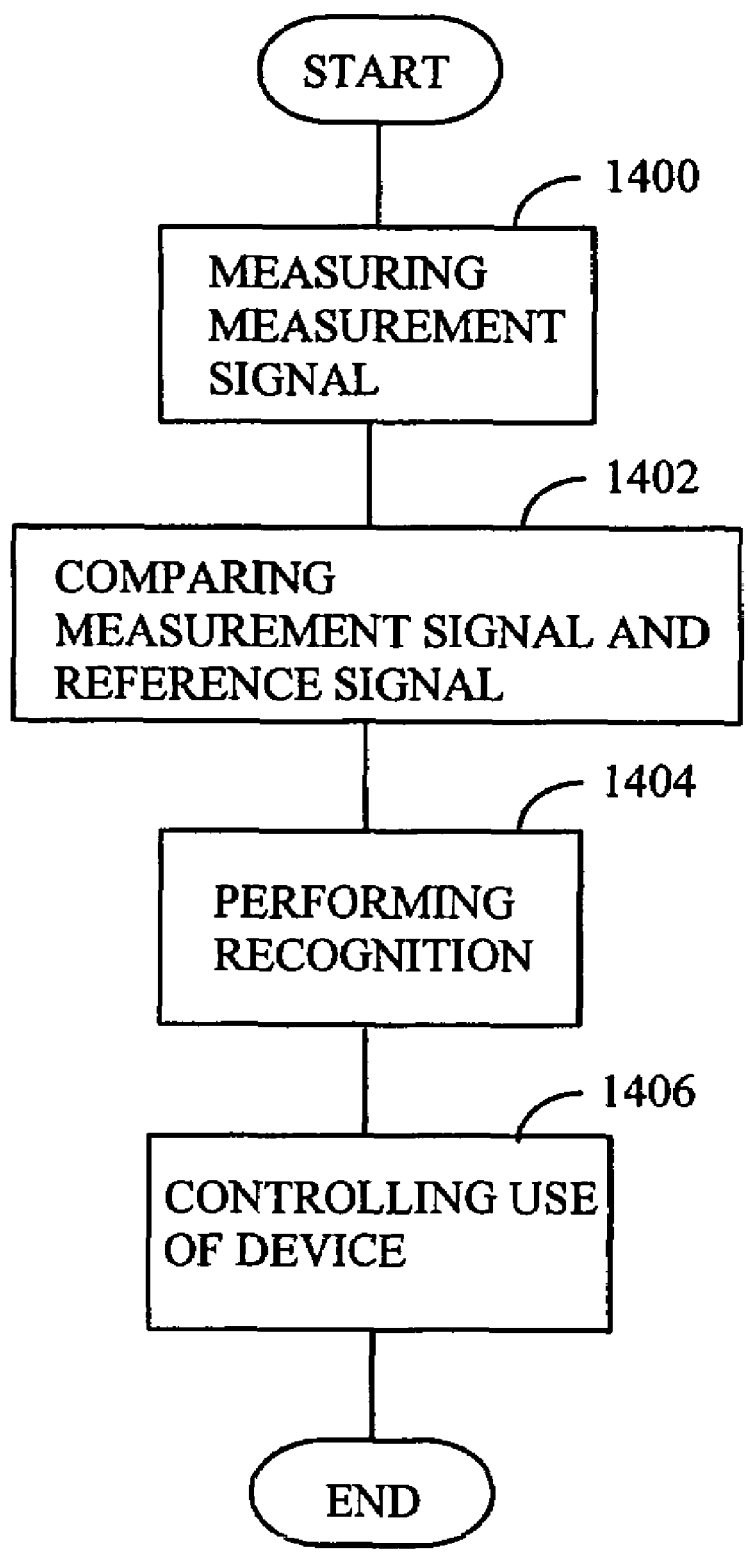
FIG. 14 illustrates a flow chart of a method of controlling use of a device relating to a living object which is moving.

FIG. 14 shows a flow chart of a method of controlling use of a device relating to a living object which is moving. In step 1400, movement of at least one user is measured by a movement sensor carried by one user at a time for forming at least one movement signal per one living object. In step 1402, the at least one movement signal is compared with at least one predetermined reference signal. In step 1404, a recognition operation based on the comparison between the at least one movement signal and the at least one predetermined reference signal is performed, the recognition operation resulting in recognition or non-recognition of the living object. In step 1406, the use of the device is controlled by the living object based on the result of the recognition operation.

Embodiments of the invention may be realized in an electronic device or system. The embodiments may be implemented as a computer program comprising instructions for executing a computer process for forming signals for recognizing a living object which is moving. The process comprises the steps illustrated in FIG. 12.

The embodiments of the invention may be realized in an electronic device or system. The embodiments may be implemented as a computer program comprising instructions for executing a computer process for performing a recognition operation relating to a living object which is moving. The process comprises the steps illustrated in FIG. 13.

The embodiments of the invention may be realized in an electronic device or system. The embodiments may be implemented as a computer program comprising instructions for executing a computer process for controlling the use of a device relating to a living object which is moving. The process comprises the steps illustrated in FIG. 14.

The computer program may be stored on a computer program distribution medium readable by a computer or a processor. The computer program medium may be, for example but not limited to, an electric, magnetic, optical, infrared or semiconductor system, device or transmission medium. The medium may be a computer readable medium, a program storage medium, a record medium, a computer readable memory, a random access memory, an erasable programmable read-only memory, a computer readable software distribution package, a computer readable signal, a computer readable telecommunications signal, or a computer readable compressed software package.

Even though the invention has been described above with reference to an example according to the accompanying drawings, it is clear that the invention is not restricted thereto but it can be modified in several ways within the scope of the appended claims.

The invention claimed is:

1. A method of identifying a carrier of a portable device, the method comprising:
identifying a carrier of a device by analyzing using a computer a measurement signal provided by an acceleration sensor of the device carried by the carrier, identification and signal analysis between the measurement signal from the acceleration sensor and a reference signal being based on at least one of the following: cross correlation, Fourier coefficients, structural pattern recognition; and
the identification and the signal analysis comprising comparing the measurement signal from the acceleration sensor with a plurality of reference signals, consecutive reference signals being shifted with respect to each other by a predetermined offset for the comparison and the plurality of reference signals and the measurement signal being shifted with respect to each other by a predetermined offset for the comparison.

2. The method of claim 1, the method being based on an analysis of a gait code of the carrier formed by at least one acceleration sensor, the analysis being carried out in the portable device.

3. The method of claim 1, wherein the identification and the signal analysis between the signal from the acceleration sensor and the reference signals being further based on amplitude histogram features.

4. A method of forming signals for recognizing a living object which is moving, the method comprising:
measuring movement of at least one predetermined living object by at least one movement sensor carried by one living object at a time for forming a plurality of reference signals per one living object;
measuring movement of at least one living object by the at least one movement sensor carried by one living object at a time for forming at least one measurement signal per one living object;
comparing said at least one measurement signal with said plurality of reference signals, consecutive reference signals being shifted with respect to each other by a predetermined offset for comparison; and
shifting the plurality of reference signals and the at least one measurement signal with respect to each other by a predetermined offset for the comparison.

5. The method of claim 4, the method further comprising:
dividing, when measuring a reference signal, a signal received from the movement sensor into partial signals each relating to different movements, forming an averaged signal of each movement, concatenating the averaged signals in the reference signal, and normalizing the reference signal; and
dividing, when measuring a measurement signal, a signal received from the movement sensor into partial signals each relating to different movements, forming an averaged signal of each movement, concatenating the averaged signals in the measurement signal, and normalizing the measurement signal.

6. The method of claim 4, the method further comprising performing the measurement of movement of each living object in at least two dimensions for including two-dimensional information in the measurement.

7. The method of claim 4, the method further comprising performing the measurement of movement as a measurement of acceleration as a function of time.

8. The method of claim 4, the method further comprising storing the plurality of reference signals in a portable device carried by the living object.

9. The method of claim 4, the method further comprising storing the plurality of reference signals in a remote device not carried by the living object.

10. A method of performing a recognition operation relating to a living object which is moving, the method comprising:
measuring movement of at least one living object by a movement sensor carried by one living object at a time for forming at least one measurement signal per one living object;
comparing the at least one measurement signal with a plurality of predetermined reference signals using a computer, consecutive reference signals being shifted with respect to each other by a predetermined offset for the comparison;
shifting the plurality of reference signals and the at least one measurement signal with respect to each other by a predetermined offset for the comparison; and
performing a recognition operation based on the comparison between the at least one measurement signal and the plurality of predetermined reference signals, the recognition operation resulting in recognition or non-recognition.

11. The method of claim 10, the method further comprising recognising the living object in the recognition operation as one of the following: a desired living object, an undesired living object, a non-recognised living object.

12. The method of claim 10, the method further comprising dividing a signal received from the movement sensor into partial signals each relating to different movements, forming an averaged signal of each movement, concatenating the averaged signals in the measurement signal, and normalizing the measurement signal.

13. The method of claim 10, further comprising determining a living object having at least one measurement signal that provides a largest similarity with the plurality of reference signals of a desired living object as a desired living object.

14. The method of claim 13, the method further comprising performing the determination if the similarity is greater than a predetermined threshold.

15. The method of claim 10, further comprising determining a living object having at least one measurement signal that provides a largest similarity with the plurality of reference signals of an undesired living object as an undesired living object.

16. A method of controlling use of a device relating to a living object which is moving, the method comprising:
   measuring movement of at least one user by a movement sensor carried by one user at a time for forming at least one movement signal per living object;
   comparing the at least one movement signal with a plurality of predetermined reference signals using a computer, consecutive reference signals being shifted with respect to each other by a predetermined offset for the comparison;
   shifting the plurality of reference signals and the at least one movement signal with respect to each other by a predetermined offset for the comparison;
   performing a recognition operation based on the comparison between the at least one movement signal and the at plurality of predetermined reference signals, the recognition operation resulting in recognition or non-recognition of the living object; and
   controlling the use of the device by the living object based on the result of the recognition operation.

17. The method of claim 16, the method further comprising restricting the use of the device in relation to the movement sensor if the recognition operation results in non-recognition or in recognition of an undesired living object, the device being a portable device or a remote device separate from the portable device.

18. The method of claim 17, the method further comprising shifting the plurality of reference signals and the measurement signal with respect to each other by a predetermined offset for the comparison.

19. The method of claim 17, further comprising determining a living object having at least one measurement signal that provides a largest similarity with the plurality of reference signals of a desired living object as a desired living object.

20. The method of claim 19, the method further comprising performing the determination if the similarity is greater than a predetermined threshold.

21. The method of claim 17, further comprising determining a living object having at least one measurement signal that provides a largest similarity with the plurality of reference signals of an undesired living object as an undesired living object.

22. The method of claim 16, the method further comprising dividing a signal received from the movement sensor into partial signals each relating to different movements, forming an averaged signal of each movement, concatenating the averaged signals in the measurement signal, and normalizing the measurement signal.

23. A portable device carried by a carrier, the device comprising:
   an acceleration sensor providing an acceleration signal of the carrier;
   a recognizer configured to identify the carrier of the device by comparing a difference between a measurement signal provided by the acceleration sensor and a plurality of reference signals, consecutive reference signals being shifted with respect to each other by a predetermined offset for the comparison, and the plurality of reference signals and the measurement signal being shifted with respect to each other by a predetermined offset for the comparison, identification and analysis of the signal being based on at least one of the following: cross correlation, Fourier coefficients, structural pattern recognition.

24. The portable device of claim 23, wherein the recognizer is configured to identify the carrier on the basis of an analysis of a gait code of the carrier formed by at least one acceleration sensor, the analysis being carried out in the recognizer.

25. The method of claim 23, wherein the identification and the signal analysis between the signal from the acceleration sensor and the reference signals being further based on amplitude histogram features.

26. A portable device carried by a moving carrier, the device comprising:
   a movement sensor configured to measure movement of each predetermined living object of at least one living object by the movement sensor carried by the one living object at a time for forming a plurality of reference signals per one living object;
   said movement sensor being configured to measure movement of each living object of at least one living object by the movement sensor carried by one living object at a time for forming at least one measurement signal per one living object, said device being configured to compare said at least one measurement signal with said plurality of reference signals, consecutive reference signals being shifted with respect to each other by a predetermined offset for comparison, and the plurality of reference signals and the at least one measurement signal being shifted with respect to each other by a predetermined offset for the comparison; and
   memory for storing the plurality of reference signals.

27. The portable device of claim 26, wherein the portable device includes a filter configured to divide, during measurement of a reference signal, a signal received from the movement sensor into partial signals each relating to different movements, to form an averaged signal of each movement, and to concatenate the averaged signals in a reference signal;
   the filter is configured to divide, during measurement of a measurement signal, a signal received from the movement sensor into partial signals each relating to different movements, to form an averaged signal of each movement, and to concatenate the averaged signals in a measurement signal; and
   the filter is configured to normalize the reference signal and the measurement signal.

28. The portable device of claim 27, wherein the filter is configured to shift consecutive reference signals of the plurality of reference signals with respect to each other by said predetermined offset for comparison.

29. The portable device of claim 26, wherein the movement sensor is configured to measure movement of each living object in at least two-dimensions for including two dimensional information per one living object in the measurement.

30. The portable device of claim 26, wherein the movement sensor is configured to measure acceleration as a function of time.

31. The portable device of claim 26, wherein the portable device includes a recogniser and a controller;
the recogniser is configured to perform a recognition operation based on the comparison between the at least one movement signal and the at least one predetermined reference signal, the recognition operation resulting in recognition or non-recognition of the user; and
the controller configured to control the use of the device based on the result of the recognition operation.

32. The portable device of claim 31, wherein the recogniser is configured to determine a living object having at least one measurement signal that provides a largest similarity with the plurality of reference signals of a desired living object as a desired living object.

33. The portable device of claim 32, wherein the recogniser is configured to perform the determination if the similarity is greater than a predetermined threshold.

34. The portable device of claim 31, wherein the recogniser is configured to determine a living object having at least one measurement signal that provides a largest similarity with the plurality of reference signals of an undesired living object as an undesired living object.

35. The portable device of claim 31, wherein the controller is configured to restrict the use of the portable device in relation to the movement sensor, if the recognition operation results in non-recognition or in recognition of an undesired user.

36. A system including a portable device carried by a moving carrier, the device comprising:
at least one movement sensor configured to measure movement of each predetermined living object of at least one living object by a movement sensor carried by one living object at a time for forming a plurality of reference signals per one living object; and configured to measure movement of each living object of at least one living object by a movement sensor carried by one living object at a time for forming at least one measurement signal per one living object, said device being configured to compare said at least one measurement signal with said plurality of reference signals, consecutive reference signals being shifted with respect to each other by a predetermined offset for comparison, and the plurality of reference signals and the at least one measurement signal being shifted with respect to each other by a predetermined offset for the comparison.

37. The system of claim 36, wherein the system includes a memory configured to store at least one reference signal, the memory being situated in a separate device not carried by the living object.

38. The system of claim 36, wherein the system includes a filter external to the portable device configured to divide a reference signal received from the movement sensor into partial signals each relating to different movements, to form an averaged signal of each movement, and to concatenate the averaged partial signals into a reference signal; and
the filter external to the portable device configured to divide a measurement signal received from the movement sensor into partial signals each relating to different movements, to form an averaged signal of each movement, and to concatenate the averaged partial signals into a measurement signal.

39. The system of claim 36, wherein the system includes a recogniser and a controller;
the recogniser being configured to perform a recognition operation based on the comparison between the at least one measurement signal and the plurality of predetermined reference signals, the recognition operation resulting in recognition or non-recognition of the user; and
the controller being configured to control the use of at least one device included in the system based on the result of the recognition operation.

40. The system of claim 39, wherein the recogniser is configured to determine a living object having at least one measurement signal that provides a largest similarity with the plurality of reference signals of a desired living object as a desired living object.

41. The system of claim 40, wherein the recogniser is configured to perform the determination if the similarity is greater than a predetermined threshold.

42. The system of claim 39, wherein the recogniser is configured to determine the living object having at least one measurement signal that provides a largest similarity with the plurality of reference signals of an undesired living object as an undesired living object.

43. The system of claim 36, wherein the controller is configured to restrict the use of the portable device including a movement sensor if the recognition operation results in non-recognition or recognition of an undesired carrier.

44. The system of claim 36, wherein the controller is configured to restrict the use of the remote device separate from the portable device, if the recognition operation results in recognition of an undesired carrier or non-recognition of the carrier.

45. A computer readable storage medium readable by a computer encoding a computer program of instructions for executing a computer process for forming signals for recognizing a living object which is moving, the process comprising:
measuring movement of at least one predetermined living object by at least one movement sensor carried by one living object at a time for forming a plurality of reference signals per one living object;
measuring movement of at least one living object by the at least one movement sensor carried by one living object at a time for forming at least one measurement signal per one living object;
comparing said at least one measurement signal with said plurality of reference signals, consecutive reference signals being shifted with respect to each other by a predetermined offset for comparison, and
shifting the plurality of reference signals and the at least one measurement signal with respect to each other by a predetermined offset for the comparison.

46. A computer readable storage medium readable by a computer encoding a computer program of instructions for executing a computer process for performing a recognition operation relating to a living object which is moving, the process comprising:
measuring movement of at least one living object by a movement sensor carried by one living object at a time for forming at least one movement signal per one living object;
comparing the at least one movement signal with a plurality of predetermined reference signals, consecutive reference signals being shifted with respect to each other by a predetermined offset for comparison;
shifting the plurality of reference signals and the at least one movement signal with respect to each other by a predetermined offset for the comparison; and performing a recognition operation based on the comparison between the at least one movement signal and the plurality of predetermined reference signals, the recognition operation resulting in recognition or non-recognition.

47. A computer readable storage medium readable by a computer encoding a computer program of instructions for executing a computer process for controlling the use of a device relating a living object which is moving, the process comprising:

measuring movement of at least one user by a movement sensor carried by one user at a time for forming at least one movement signal per one user;

comparing the at least one movement signal with a plurality of predetermined reference signals, consecutive reference signals being shifted with respect to each other by a predetermined offset for comparison;

shifting the plurality of reference signals and the at least one movement signal with respect to each other by a predetermined offset for the comparison performing a recognition operation based on the comparison between the at least one movement signal and the plurality of predetermined reference signals, the recognition operation resulting in recognition or non-recognition of the user; and controlling the use of the device based on the result of the recognition operation.

48. A computer readable storage medium readable by a computer and encoding a computer program of instructions for executing a computer process for forming signals for recognizing a living object which is moving, the process comprising:

measuring movement of at least one predetermined living object by at least one movement sensor carried by one living object at a time for forming at least one reference signal per one living object;

measuring movement of at least one living object by the at least one movement sensor carried by one living object at a time for forming at least one measurement signal per one living object;

comparing said at least one measurement signal with said plurality of reference signals, consecutive reference signals being shifted with respect to each other by a predetermined offset for comparison; and shifting the plurality of reference signals and the at least one measurement signal with respect to each other by a predetermined offset for the comparison.

49. The computer readable storage medium of claim 48, including at least one of the following mediums: a computer readable medium, a program storage medium, a record medium, a computer readable memory, a computer readable software distribution package, a computer readable signal, a computer readable telecommunications signal, and a computer readable compressed software package.

50. A computer readable storage medium readable by a computer and encoding a computer program of instructions for executing a computer process for performing a recognition operation relating to a living object which is moving, the process comprising:

measuring movement of at least one living object by a movement sensor carried by one living object at a time for forming at least one movement signal per one living object;

comparing the at least one movement signal with a plurality of predetermined reference signals, consecutive reference signals being shifted with respect to each other by a predetermined offset for comparison;

shifting the plurality of reference signals and the at least one movement signal with respect to each other by a predetermined offset for the comparison; and performing a recognition operation based on the comparison between the at least one movement signal and the plurality of predetermined reference signals, the recognition operation resulting in recognition or non-recognition.

51. A computer readable storage medium readable by a computer and encoding a computer program of instructions for executing a computer process for controlling the use of a device carried by a moving user, the process comprising:

measuring movement of at least one user by a movement sensor carried by one user at a time for forming at least one movement signal per one user;

comparing the at least one movement signal with a plurality of predetermined reference signals, consecutive reference signals being shifted with respect to each other by a predetermined offset for comparison;

shifting the plurality of reference signals and the at least one movement signal with respect to each other by a predetermined offset for the comparison;

performing a recognition operation based on the comparison between the at least one movement signal and the plurality of predetermined reference signals, the recognition operation resulting in recognition or non-recognition of the user; and controlling the use of the device based on the result of the recognition operation.

* * * * *